United States Patent [19]

Briar et al.

[11] 4,074,563

[45] Feb. 21, 1978

[54] IN-SITU MEASUREMENT APPARATUS

[75] Inventors: Herman P. Briar, Rancho Cordova; Kenneth W. Bills, Jr., Sacramento, both of Calif.

[73] Assignee: The United States of America as represented by the Secretary of the Air Force, Washington, D.C.

[21] Appl. No.: 731,484

[22] Filed: Oct. 12, 1976

[51] Int. Cl.$^2$ .................................... G01N 33/22
[52] U.S. Cl. .................................. 73/35; 340/207 R; 340/224
[58] Field of Search .......... 73/35, 88 R, 88 C, 88.5 R; 340/213 R, 224, 201 R, 207 R

[56] References Cited

U.S. PATENT DOCUMENTS

| | | | |
|---|---|---|---|
| 3,270,564 | 9/1966 | Evans | 73/88.5 R X |
| 3,806,905 | 4/1974 | Strenglein | 340/224 |
| 3,937,070 | 2/1976 | Briar | 73/88 R |

*Primary Examiner*—James J. Gill
*Attorney, Agent, or Firm*—Joseph E. Rusz; William Stepanishen

[57] ABSTRACT

This is an in-situ telemetry apparatus for the measurement of dynamic moduli, a key design parameter, of the propellant mass of solid fuel rocket engines.

10 Claims, 4 Drawing Figures

(a) ZENER DIODE FOR REFERENCE VOLTAGE (b) MINATURE BATTERIES FOR REFERENCE VOLTAGE $L_1$ = 30 TURNS #30 WIRE WOUND OVER 10Ω RESISTOR
$L_2$ = 5 TURNS #30 WIRE 0.2" DIA. 0.3" LONG
$R_b$ = FROM 10,000 Ω TO 20,000 Ω TO OBTAIN 1.2VDC AT POINT O RESISTANCE IN OHMS

4,074,563

IN-SITU MEASUREMENT APPARATUS

STATEMENT OF GOVERNMENT INTEREST

The invention described herein may be manufactured and used by or for the Government for governmental purposes without the payment of any royalty thereon.

BACKGROUND OF THE INVENTION

The present invention relates broadly to a measurement apparatus, and in particular to a modulus sensing apparatus which is implanted in a propellant's state.

There is currently need for support devices capable of sensing the dynamic properties of propellant masses over long time periods without disturbing the integrity of the propellant charge. Should the properties of the propellant mass change significantly then the operational capability of the rocket motor might be impaired. The invention was devised to monitor the propellant mass as it stands, while encased within the rocket motor, so that a nondestructive assessment of the propellant properties might be determined.

The invention was devised to work in conjunction with an active sensor (U.S. Pat. No. 3,937,070) which is capable of measuring dynamic moduli while encased in soft plastic, soil, asphalt, rubber, or propellant. Wireless telemetry is desired in many instances due to the nature of the placement; e.g., hard-wired devices in a ready-to-operate rocket motor might create a hazard or moderate the mission of the rocket.

The active sensors require external power input (by inductance) which effects the internal operation of the sensor and, in turn, the telemetry of data obtained from the sensor measurements.

SUMMARY

The present invention utilizes a dynamic sensor which is embedded within a propellant to sense and transmit information relating to dynamic modulus. An oscillator provides a time-varying voltage to a deformable sensing element the deformity of which is detected and measured to provide useful stress-to-strain relationships. The deformation information is transmitted from within the propellant to an adjacent external receiver.

It is one object of the present invention, therefore, to provide an in-situ measurement apparatus capable of providing data concerning dynamic moduli of propellant masses.

It is another object of the invention to provide an improved in-situ measurement apparatus having a sensing element embedded within the propellant mass of a solid fuel rocket engine.

It is yet another object of the invention to provide an improved in-situ measurement apparatus wherein the data from the embedded sensor is transmitted to an external receiver for processing.

These and other advantages, objects and features of the invention will become more apparent from the following description taken in connection with the illustrative embodiment in the accompanying drawings.

DESCRIPTION OF THE PREFERRED EMBODIMENT

Figure 1:
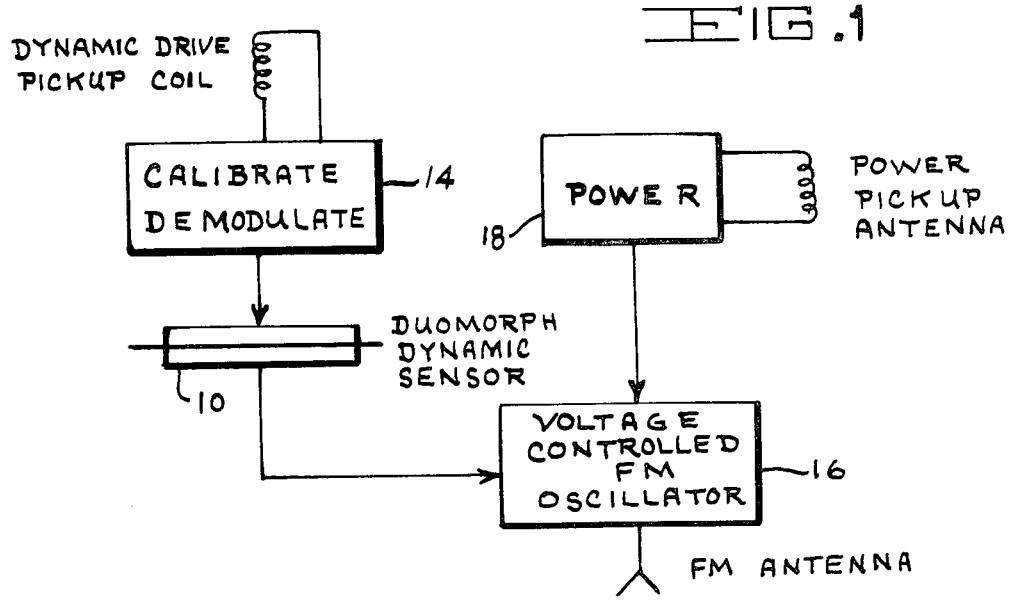
FIG. 1 is a block diagram of the in-situ measurement apparatus in accordance with the present invention.

Referring now to FIG. 1, there is shown a block diagram of the in-situ measurement apparatus utilizing a duomorph dynamic sensor 10 as the sensing element which may be embedded in the propellent mass of a solid fuel rocket engine. There is connected to the duomorph dynamic sensor 10, a calibrate-demodulate unit 14 which has a pickup coil attached thereto to receive a dynamic drive signal from an external source. The output data from the duomorph dynamic sensor 10 is applied to a voltage-controlled FM oscillator 16. A power unit 18 which has a power pickup antenna to receive power from an external power source, is connected to the voltage-controlled FM oscillator 16. The voltage-controlled FM oscillator 16 has an FM antenna attached thereto, to permit transmission of output data from the duomorph dynamic sensor unit 10 to a remote receiver.

The basic operation of the in-situ measurement apparatus begins with a voltage from the calibrate-dimodulate unit 14 which is applied to one side of the duomorph sensor 10. The duomorph sensor 10 is deformed in response thereto, this deformation is sensed by the sensing element on the opposed side. The power to operate the unit and the modulation information to control it are extracted from an RF field that is established in the propellant in which the apparatus is embedded, from an external antenna (not shown). A voltage controlled oscillator 16 transmits information on the deformation of the duomorph sensor 10 to an external FM receiver (not shown) and from there to an oscilloscope display.

Figure 2:
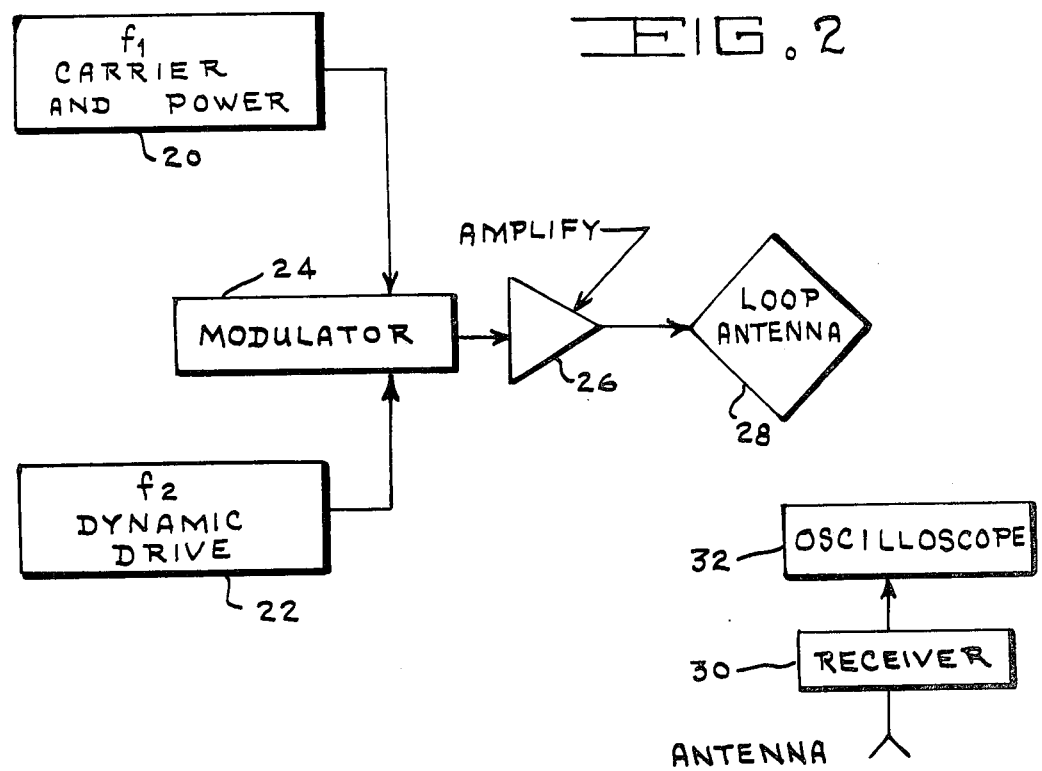
FIG. 2 is a block diagram of the external power and detection apparatus for the in-situ measurement apparatus, FIGS. 3a and 3b respectively are schematic diagrams of the power supply circuit for the in-situ measurement apparatus, and, FIG. 4 is a schematic diagram of the oscillator circuit of the present invention.

Turning now to FIG. 2, there is shown a block diagram of the external power and detection apparatus which provides the RF field and the excitation means to power the in-situ measurement apparatus that is imbedded in the solid propellant mass. A first carrier frequency generator and power source unit 20 generates a first carrier frequency, $f_1$, which is the A.C. power to drive the calibrate-demodulate unit 14 of FIG. 1. A second carrier frequency generator unit 22 generates a second carrier frequency, $f_2$, which is the dynamic drive that is received and utilized by the duomorph sensor 10 of FIG. 1. The outputs from the first and second carrier frequency generator units 20, 22 are applied to modulator unit 24 wherein both signals are modulated and applied to the amplifier unit 26. The modulated signal from the amplifier unit 26 is radiated to the in-situ measurement apparatus by means of loop antenna 28.

The carrier and power operate at the frequency, $f_1$, which is near 200 khz. The dynamic drive frequency, $f_2$, is in the range 5 to 4000 hz. The frequency $f_2$ modulates the carrier and the modulated carrier is amplified and fed to a loop antenna 28 where a 25 watt RF field is established. An external FM receiver 30 picks up output signals from voltage-controlled FM oscillator which are displayed on an oscilloscope 32. The displayed data may be recorded from the oscilloscope by a camera which may be attached thereto.

Figure 3:
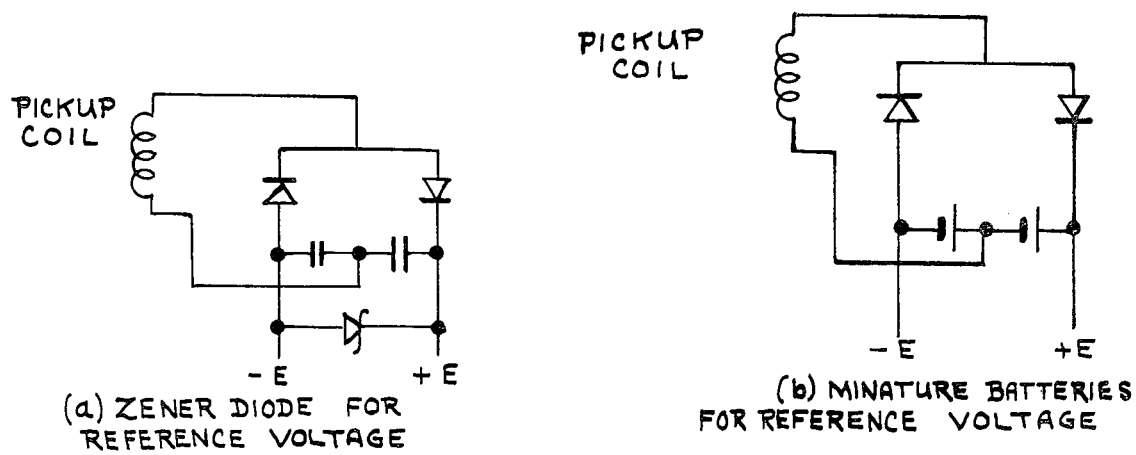

There is shown in FIGS. 3a and 3b respectively a schematic diagram of power source for the in-situ measurement apparatus. The power source in FIG. 3a is basically a standard A.C. powered D.C. source except for the ferrite rod with a coil wound thereon to form the pickup coil. An alternate circuit replaces the capacitors and the zener diode with miniature rechargeable nickel cadmium batteries, as shown in FIG. 3b. The power module is capable of furnishing 3 ma at 2.5 volts within a 3 foot range from the center of the external power loop antenna. The power module is 2 inches long and 1.25 inches in diameter.

Figure 4:
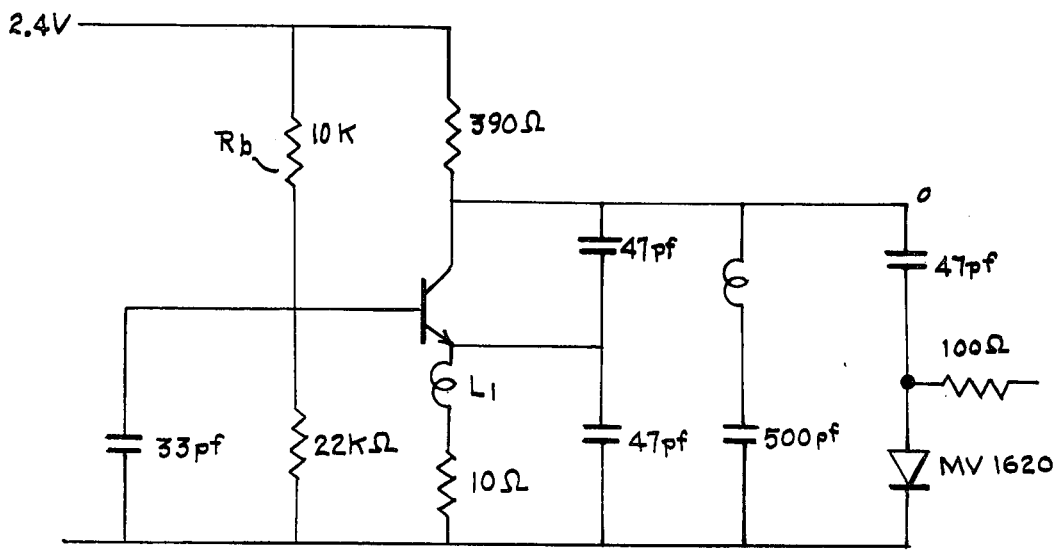

The FM voltage controlled oscillator which is shown schematically in FIG. 4 accepts an analog AC or DC voltage and converts this voltage to a frequency deviation which can be sensed by an FM receiver. The oscillator dimensions are 1.25 inches diameter × 0.4 inches thick. It requires 3 ma at 2.5 volts for optimum operation. However, it will operate over the range between 2.0 and 3.0 volts. The oscillator also requires its own antenna. This antenna may be a 4 inch piece of wire which must not be in electrical contact with the propellant; e.g., bare copper wire in propellant will not work. One method for insulating the antenna was to encase it in ¼ in. plastic tubing. The values which are shown in FIG. 4 are typically values that may be varied to provide operation at a different frequency. The following component values are utilized in the present circuit:

$L_1$ = 30 turns #30 wire wound over 10Ω resistor, $L_2$ = 5 turns #30 wire 0.2 inches dia. 0.3 inches long, and $R_b$ is varied from 10,000Ω to 20,000Ω to obtain 1.2V DC at point 0 resistance in ohms.

Although the invention has been described with reference to a particular embodiment, it will be understood to those skilled in the art that the invention is capable of a variety of alternative embodiments within the spirit and scope of the appended claims.

What is claimed is:

1. An in-situ measurement apparatus for solid fuel rocket engines comprising in combination:
   an excitation means generating a power signal and dynamic drive signal, said power signal and said dynamic drive signal being combined to provide an R.F. field, said R.F. field being radiated by said excitation means,
   a sensing means embedded in the propellant mass of a solid fuel rocket engine, said sensing means receiving said R.F. field, said sensing means extracting said power signal and said dynamic drive signal from said R.F. field, said sensing means utilizing said dynamic drive signal to provide a data signal, said sensing means utilizing said power signal to modulate said data signal, said sensing means transmitting said modulated data signal, and,
   a signal processing means to receive said modulated data signal, said signal processing means demodulating said modulated data signal to provide said data signal, said data signal representing the state of said propellent mass.

2. An in-situ measurement apparatus as desceibed in claim 1 wherein said excitation means comprises in combination:
   a first carrier frequency generator unit to provide a first carrier frequency, said first carrier frequency being a power signal,
   a second carrier frequency generator unit to provide a second carrier frequency, said second carrier frequency being a dynamic drive signal,
   a modulator unit receiving said first and second carrier frequency from said first and second carrier frequency generator units, said modulator unit modulating said first carrier frequency with said second carrier frequency to provide a modulated output, and
   an amplifier unit to receive said modulated output, said amplifier amplifying said modulated output, said amplifier applying said amplified modulated output to a loop antenna, said loop antenna radiating said amplifier modulated output to provide an R.F. field.

3. An in-situ measurement apparatus as described in claim 1 wherein said sensing means comprises in combination:
   a demodulator unit to receive said R.F. field to extract said dynamic drive signal therefrom, said demodulator providing said dynamic drive signal as an output therefrom.
   a dynamic sensor to receive said dynamic drive signal, said dynamic sensor responding to said dynamic drive signal by providing a data signal,
   a power unit to receive said R.F. field to extract said power signal therefrom, said power unit providing said power signal as an output therefrom, and,
   an F.M. oscillator to receive both said data signal and said power signal, said F.M. oscillator modulating said data signal to provide a modulated data signal, said F.M. oscillator applying said modulated data signal to an F.M. antenna, said modulated data signal being radiated from said F.M. antenna.

4. An in-situ measurement apparatus as described in claim 1 wherein said signal processing means comprises in combination: an F.M. receive antenna and receiver, said modulated data signal being received by said F.M. receive antenna and being applied thereby to said F.M. receiver, said F.M. receiver demodulating said modulated data signal to provide said data signal.

5. An in-situ measurement apparatus as described in claim 1 wherein said R.F. field has a power level of 25 watts.

6. An in-situ measurement apparatus as described in claim 4 further including a display means connected to said F.M. receiver, said display means providing a visual display of said data signal.

7. An in-situ measurement apparatus as described in claim 3 wherein said dynamic sensor comprises a duomorph dynamic sensing element.

8. An in-situ measurement apparatus as described in claim 3 wherein said F.M. oscillator comprises a voltage-controlled F.M. oscillator.

9. An in-situ measurement apparatus as described in claim 6 wherein said display means comprises an oscilloscope to display said data signal.

10. An in-situ measurement apparatus as described in claim 6 further including a recording means connected to said display means to provide a permanent record of said data signal.

* * * * *